(12) United States Patent
Sander

(10) Patent No.: US 6,543,914 B2
(45) Date of Patent: Apr. 8, 2003

(54) STAND ARRANGEMENT

(75) Inventor: Ulrich Sander, Rebstein (CH)

(73) Assignee: Leica Microsystems AG, Heerbrugg (CH)

(*) Notice: Subject to any disclaimer, the term of this patent is extended or adjusted under 35 U.S.C. 154(b) by 0 days.

(21) Appl. No.: 09/940,732

(22) Filed: Aug. 28, 2001

(65) Prior Publication Data

US 2002/0064048 A1 May 30, 2002

(30) Foreign Application Priority Data

Aug. 29, 2000 (DE) .......................... 100 42 272

(51) Int. Cl.$^7$ ............................... F21V 21/20
(52) U.S. Cl. ................. 362/401; 362/575; 362/402; 362/419; 248/280.11; 359/390
(58) Field of Search ................. 362/572, 574, 362/575, 401, 402, 414, 551, 33, 35; 359/388, 390–393; 248/123.11, 182.1, 280.11

(56) References Cited

U.S. PATENT DOCUMENTS

| | | | | |
|---|---|---|---|---|
| 3,428,797 A | * | 2/1969 | Haynes | 362/572 |
| 3,790,249 A | * | 2/1974 | Treace | 359/388 |
| 3,790,773 A | * | 2/1974 | Sapper | 362/401 |
| 5,213,293 A | | 5/1993 | Muentener et al. | 248/123.1 |
| 6,050,688 A | * | 4/2000 | Grinblat | 351/214 |
| 6,129,319 A | | 10/2000 | Metelski | 248/123.2 |
| 6,247,673 B1 | | 6/2001 | Bees | 248/123.11 |

OTHER PUBLICATIONS

Carl Zeiss Surgical Products Division, "The Benchmark in Ophthalmic Surgery—The VISU 200 & S8 Floorstand", Ophthalmic Product Guide, vol. 5, Feb. 1999.

* cited by examiner

*Primary Examiner*—Alan Cariaso
*Assistant Examiner*—Ali Alavi
(74) *Attorney, Agent, or Firm*—Hodgson Russ LLP

(57) ABSTRACT

Stand arrangement, in particular for medical examining and surgical microscopes, having a support foot (1), an upper part (2a), which can be rotated with respect to the support foot (2) about a vertical axis (A), and a boom (3), mounted pivotably thereon, for holding the microscope (9). The lamp housing (11) is arranged on a carrier (10) connected to the boom (3) and thereby serves to balance the stand.

14 Claims, 2 Drawing Sheets

STAND ARRANGEMENT

CROSS REFERENCE TO RELATED APPLICATIONS

This invention claims priority of the German patent application 100 42 272.1 filed Aug. 29, 2001 which is incorporated by reference herein.

FIELD OF THE INVENTION

The invention relates to a stand arrangement, in particular for medical examining and surgical microscopes.

BACKGROUND OF THE INVENTION

Stands for medical examining and surgical microscopes are known to comprise a support foot and an upper part which cam be rotated with respect to the support foot about a first vertical axis and on which there is fastened a boom which can pivot about a horizontal axis and can be rotated about the first vertical axis and/or about a second vertical axis and serves the purpose of holding a microscope connected to it. It is further known to provide on the stand an illuminating system, having at least one lamp housing and at least one flexible optical conductor, for illuminating an object.

Stands for surgical microscopes must, on the one hand, be very mobile and capable of being effectively balanced so that the movement of the microscope can be performed with a low expenditure of force and in a very short time. On the other hand, the stand must be very stiff in order to permit a good image quality and to prevent shaking of the image. The relatively large overhang required by the boom for application on the operating table produces high forces and bending moments on the components and bearing points.

A relatively strong light source is required in order to illuminate the surgical site optimally. As a rule, this is integrated into a lamp housing designed as a separate component. In order for this lamp housing not to obstruct the surgeon during the operation, and also so that the heat radiated by the lamp housing does not hamper the surgeon, it is usual to arrange the lamp housing far away from the surgical microscope, for example on the support foot. The light is conducted to the surgical site by means of a flexible optical conductor. This arrangement of the lamp housing requires very long optical conductors. A very high degree of flexibility is required given that these optical conductors must be guided past the many joints of the stand.

One known stand design, the "Zeiss Visu 200 & S8", requires less flexibility. This design also has lazy tongs, which form the boom. The lazy tongs are spring-loaded by means of a bearing spring, and therefore permit balancing so that a user can operate a relatively counterbalanced microscope. In this case, "relatively counterbalanced" means that the user scarcely feels the weight of the microscope, because it is cancelled by the force of the bearing spring in the lazy tongs design. This apparent balancing is not, however, performed via weight equalization over a vertical axis of rotation or bearing axis of the stand. Rather, the load of the lazy tongs, and all the loads hanging from it—including, for example, the weight of the bearing spring and the microscope, together with accessory equipment—are absorbed in the form of bending forces on the vertical bearing axis. These bending forces lead to a tilting moment which is, in turn, absorbed by a sufficiently large and heavy support foot below the vertical bearing axis.

The greater the loads, the greater the bending forces become, and the greater the tilting moments, the larger and heavier the support foot must be. However, the larger the support foot, the less freedom of movement there is for the user during his activity in the region of the stand.

WO 9901693 A1 discloses a microscope stand in the case of which this problem is solved by installing the control, illumination, etc. on the vertical bearing axis in a region projecting away from the microscope.

A certain balancing effect, or at least a displacement of the overall centroid in the direction of the vertical bearing axis may also be yielded by the abovementioned stand design of "Zeiss Visu 200 & S8". Changes to the weight of the microscope or its accessory equipment can, however, be compensated in the case of both known solutions only by changing the spring force of the bearing spring, that is to say all the changes in weight lead to a change in the balance about the vertical bearing axis and/or to changed bending moments on the latter.

SUMMARY OF THE INVENTION

It is the object of the invention to create a stand arrangement which can be kept more effectively in the balanced state of equilibrium via the vertical bearing axis without the need in this case to increase the total weight of the stand design.

In accordance with the invention, this is achieved by virtue of the fact that a carrier for holding the lamp housing is provided on the side diametrically opposite the boom with respect to the vertical axis. Since the carrier is arranged opposite the boom, the weight of the carrier and of the lamp housing, when multiplied by the distance of their centroids from the vertical pivoting axis, yields counter-moments which oppose the torques produced on the boom. In the optimum situation, the sums of these moments cancel one another out. The support foot can therefore be made smaller, and the total weight can be designed to be the same or even smaller.

The carrier is expediently rigidly connected to the boom. This produces a two-armed lever, corresponding to a balance beam which is mounted such that it can rotate about an axis and on which the individual forces can act. The carrier and the boom can be of unipartite design, or be assembled from at least two elements.

In order to be able to adapt to the various equipment configurations of the microscope, for example by adding on different accessory parts, the lamp housing is advantageously arranged on the carrier such that it can be displaced and fixed. This displaceability can occur, for example, in stages by means of rows of holes for the fastening screws, or continuously by means of longitudinal slots.

In the simplest design, the boom can pivot on the upper part about the vertical axis of rotation of the support foot. However, it is expedient for a universal adjustability of the stand that the boom can pivot on the upper part about an axis running parallel to the vertical axis of rotation of the support foot. It is thereby possible for an intermediate link between the support foot and the boom, or upper part forming the carrier, to be pivoted away quickly if required. In this case, the upper part can be of unipartite or multipartite design.

The lamp housing containing the transformer, the incandescent bulbs and any required controllers is normally not very heavy. Consequently, in accordance with a development of the invention, fastening means for holding additional balance weights are provided on the carrier and/or on the lamp housing for more effective balancing of the stand.

Such fastening means can be, for example, guide bars on which the balance weights can be displaced and fixed as in the case of a balance beam.

Instead of, or in addition to, balance weights, it is advantageous to provide spring means for balancing between the carrier and the upper part. Such spring means can be designed, for example, as simple tension springs or as gas-pressure springs. By using them, it is possible to make the bearing spring, possibly provided on the boom, smaller, and thereby reduce the weight of the boom itself, and this in turn assists the balancing effect.

The displacement of the lamp housing and/or of the balance weights can be performed purely manually by scales or by feel. However, this procedure requires expenditure of time and a certain degree of experience or skill. However, it can occur during an operation that accessory parts of different weight and centroid distance need to be exchanged very quickly. In order that no delays or complications occur in this case, in accordance with a development of the invention, the displacement of the lamp housing and/or of the balance weights is advantageously performed via an automatic controller, as a function of the position and/or the weight of the microscope and/or its accessory equipment. The controller can be regulated, for example, via force sensors, deformation sensors, displacement sensors or angle sensors. It is also possible in this case for external forces, for example a person leaning against the stand, to be compensated.

A device for automatically balancing a stand is specified in a plurality of exemplary embodiments in U.S. Pat. No. 6,129,319 (based on WO 9713997 A1), such patent being hereby incorporated by reference into the present specification. The automatic functions for automatically balancing a stand are illustrated and described in FIGS. 1 to 6, 8 and 18 to 20 and the associated description.

BRIEF DESCRIPTION OF THE DRAWINGS

The invention is to be explained in more detail below with the aid of the symbolic drawings which reproduce it by way of example. In the drawings.

DETAILED DESCRIPTION OF THE INVENTION

Figure 1:
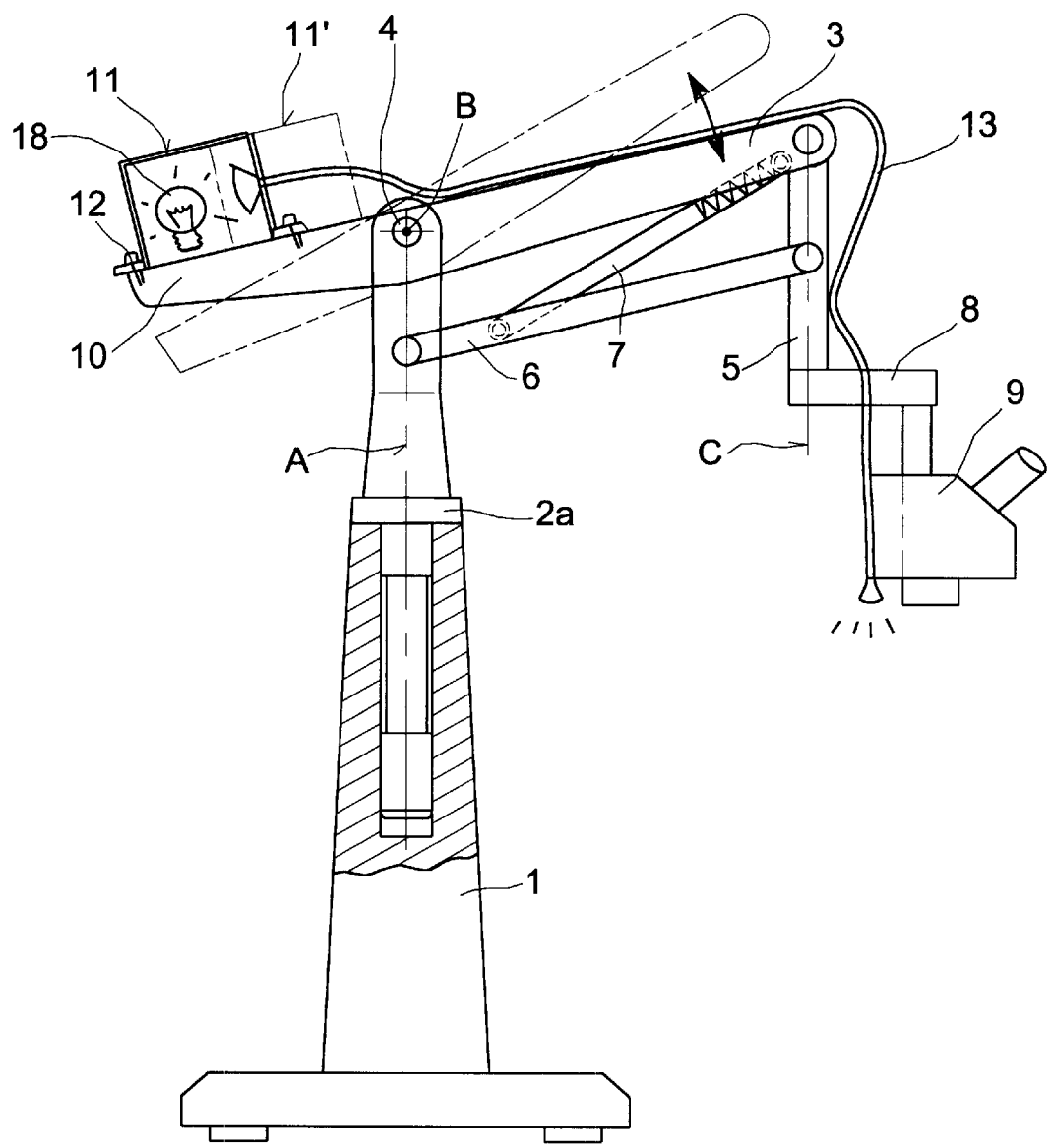
FIG. 1 shows a stand arrangement according to the invention with a boom mounted such that it can rotate about the support foot.

Corresponding parts have been provided in the figures with identical reference numerals. In this case, comparable parts have identical reference symbols with different indices.

The stand design essentially comprises a support foot 1 and an upper part 2a connected thereto. The upper part 2a is mounted such that it can rotate with respect to the support foot 1 about a vertically running axis A. A boom 3 is movably connected to the upper part 2a via a bolt 4. The bolt 4 forms a pivoting axis B running essentially horizontally. The boom 3 can therefore be moved up and down about the axis B, or the bolt 4. A vertically running support column 5 is suspended at the free end of the boom 3. A strut 6 running parallel to the boom 3 is connected in a pivoted fashion at one end to the upper part 2a, and at the other end to the support column 5. The boom 3, the strut 6, the upper part 2a and the support column 5 therefore form a parallelogram. This means that the support column 5 always remains in a vertical position independently of the position of the boom 3, as is indicated by the pivoting of the boom in the direction of the double arrow. A bearing spring, for example a gas-pressure spring 7, is provided in order to counterbalance the weight on the support column 5 and the boom 3. This design with the bearing spring corresponds approximately to the design which is known from EP 0 433 426 A1 and the "Zeiss Visu 200 & S8", and so there is no need to go into the technical details more closely.

It may be stressed that the invention is riot limited to such lazy tongs designs; rather, it also comprises boom designs without a strut 6 and gas-pressure spring 7.

A bracket 8 is located at the lower end of the support column 5. This bracket can have additional joints or adjusting mechanisms for a microscope 9 fastened thereon.

A carrier 10 is located on the side of the axis B opposite the boom 3. This carrier is preferably permanently connected to the boom 3, or of unipartite design. The carrier 10 serves to hold a lamp housing 11 for illuminating the surgical site. The lamp housing 11 is detachably connected to the carrier 10 by means of screws 12. After the loosening of the screws 1, the lamp housing 11 can thereby be displaced for the purpose of balancing the boom 3 into a different position along the carrier 10, and be fixed there again. The light, which is produced by means of incandescent lamps 18, for example, is fed to the operator's field of view via a flexible optical conductor 13. The screws 12 can be fitted (not illustrated in more detail) with handles, grips, knurled parts, wings or the like in order to simplify their manipulation. They can also be replaced within the scope of the invention by any other desired fastening means.

Figure 2:
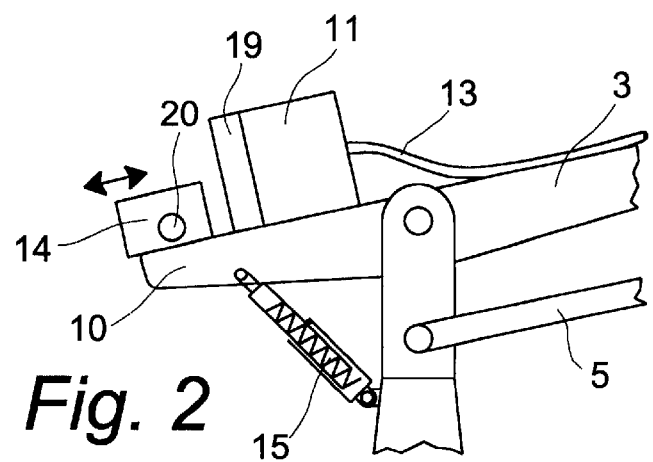
FIG. 2 shows a partial view of a stand arrangement with additional weights and spring means for balancing.

The design visible in FIG. 2 differs from the design illustrated in FIG. 1 in that, in addition to the lamp housing 11 and carrier 10, further means are provided for balancing the boom 3. This balancing can be performed optionally by additional balance weights 14, which can be fastened on the carrier 10, and/or by spring means 15 designed as tension springs or gas-pressure springs, for example. Like the lamp housing 11, as well, the balance weights 14 can be of displaceable design. This displacement is performed in the exemplary embodiment by a motor 20, via which the balance weight 14 is displaced in the direction of the double arrow along the carrier 10. The motor 20 is energized via a control device 19. The motor 20 is driven as a function of the position and the weight of the microscope 9 and its accessory parts, the position being detected with the aid of sensors (not illustrated) by the control device 19. The control device 19 is arranged in the lamp housing 11 in a particular configuration.

Figure 3:
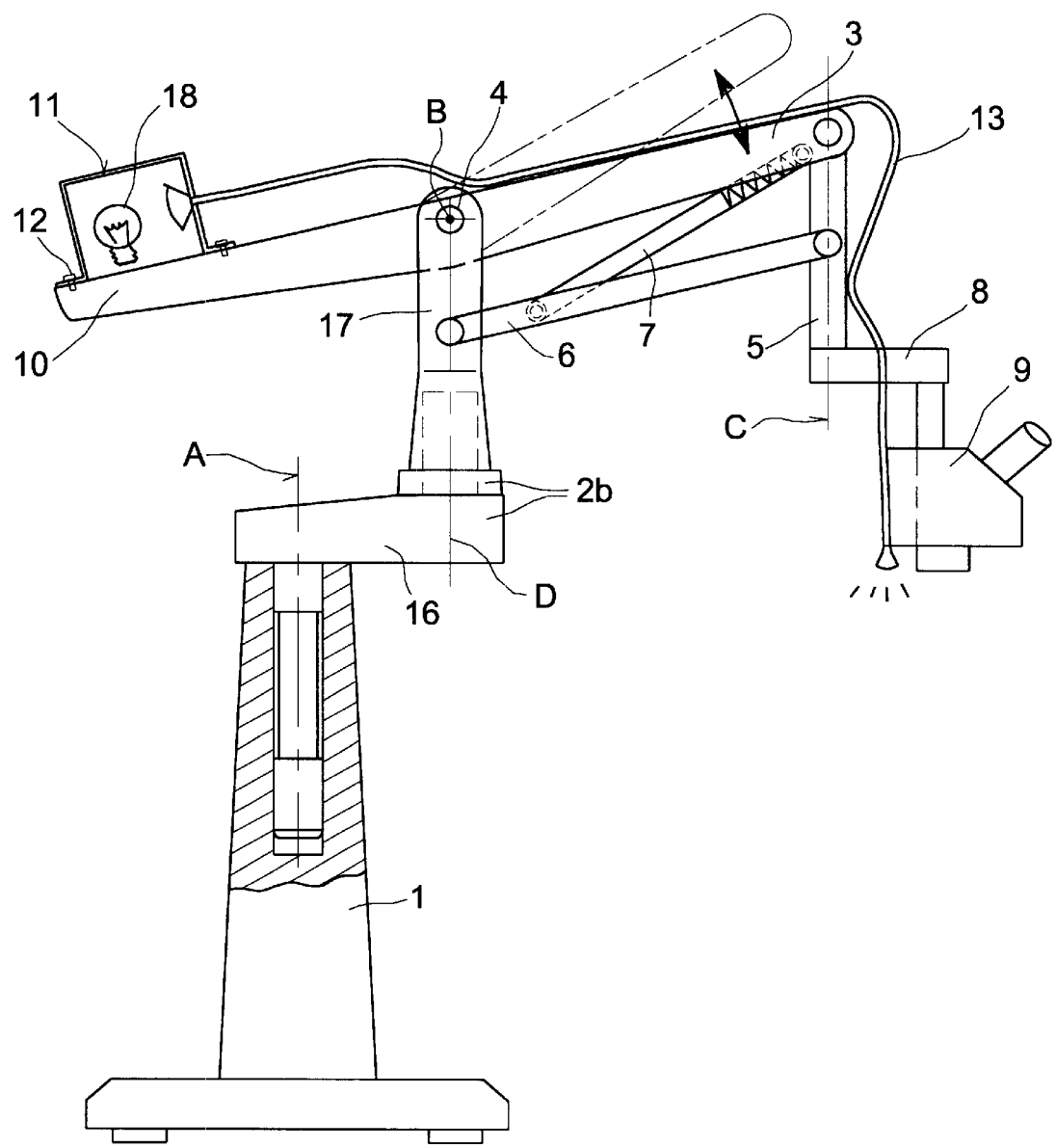
FIG. 3 shows a stand arrangement with laterally offset bearing of the boom.

In the design illustrated in FIG. 3, the upper part 2b is of bipartite design and comprises a crossbeam 16 and an upright 17 movably connected thereto. This arrangement provides an additional axis D, which runs parallel to the axis A. The upright 17 and the crossbeam 16 can therefore be rotated around the support foot 1 in the manner of a hand crank. The boom 3, connected to the upright 17, and also the carrier 10 can therefore be moved in a position running parallel to the plane of the drawing. In the case of this solution, as well, it is possible to provide further means for balancing in addition to the lamp housing 11.

In a preferred refinement of the invention, the means for balancing project beyond the axis A, as is illustrated in FIG. 1. As a result, the balancing is advantageously optimized for that stand position in which the furthest overhang of the boom 3 projects away from the axis A. The greatest risk of tilting exists for the stand in this stand position.

PARTS LIST

| | |
|---|---|
| 1 | Support foot |
| 2a, b | Upper part |
| 3 | Boom |
| 4 | Bolt |
| 5 | Support column |
| 6 | Strut |
| 7 | Gas-pressure spring |
| 8 | Bracket |
| 9 | Microscope |
| 10 | Carrier |
| 11, 11' | Lamp housing |
| 12 | Screws |
| 13 | Optical conductor |
| 14 | Balance weight |
| 15 | Spring means |
| 16 | Crossbeam |
| 17 | Upright |
| 18 | Incandescent lamp |
| 19 | Control device |
| 20 | Motor |
| A, C, D | First-third vertical axis, B horizontal axis |

What is claimed is:

1. In a stand arrangement for supporting medical examining and surgical microscopes on a stand, said stand having a support foot and an upper part which can be rotated with respect to said support foot about a first vertical axis and on which there is fastened a boom which can pivot about a horizontal axis and can be rotated about said first vertical axis and serves the purpose of holding a microscope connected to it, said stand arrangement including an illuminating system provided on said stand having at least one lamp housing and at least one flexible optical conductor for illuminating an object, the improvement comprising:
   a carrier for holding said lamp housing is provided on a side diametrically opposite said boom with respect to said first vertical axis.

2. The improvement in a stand arrangement according to claim 1, characterized in that said carrier is rigidly connected to said boom.

3. The improvement in a stand arrangement according to claim 2, wherein said carrier and said boom are portions of a unipartite component.

4. The improvement in a stand arrangement according to claim 1, wherein said lamp housing is arranged on said carrier such that it can be selectively displaced and fixed.

5. The improvement in a stand arrangement according to claim 1, wherein said boom is mounted such that it can pivot relative to said upper part about a second vertical axis which runs parallel to said first vertical axis.

6. The improvement in a stand arrangement according to claim 1, wherein said boom is mounted such that it can pivot about said first vertical axis together with said upper part.

7. The improvement in a stand arrangement according to claim 1, further comprising additional balance weights provided on said carrier and fastening means for holding said additional balance weights.

8. The improvement in a stand arrangement according to claim 7, wherein said additional balance weights are mounted on said lamp housing.

9. The improvement in a stand arrangement according to claim 7, wherein said balance weights are arranged on said carrier such that they can be displaced and fixed.

10. The improvement in a stand arrangement according to claim 1, further comprising spring means connected between said carrier and said upper part for the purpose of balancing.

11. The improvement in a stand arrangement according to claim 4, further comprising an automatic controller having a motor connected to said lamp housing, whereby displacement of said lamp housing is performed automatically.

12. The improvement in a stand arrangement according to claim 9, further comprising an automatic controller having a motor connected to said lamp housing and to said balance weights, whereby displacement of said lamp housing and said balance weights is performed automatically.

13. The improvement in a stand arrangement according to claim 5, characterized in that in at least one rotary position said carrier projects beyond both said second vertical axis and said first vertical axis such that balancing is optimized for the furthest overhang of said boom away from said first vertical axis.

14. In a stand arrangement for supporting medical examining and surgical microscopes on a stand, said stand having a support foot and an upper part which can be rotated with respect to said support foot about a first vertical axis and on which there is fastened a boom which can pivot about a horizontal axis and can be rotated about a second vertical axis and serves the purpose of holding a microscope connected to it, said stand arrangement including an illuminating system provided on said stand having at least one lamp housing and at least one flexible optical conductor for illuminating an object, the improvement comprising:
   a carrier for holding said lamp housing is provided on a side diametrically opposite said boom with respect to at least one of said first and second vertical axes.

* * * * *